United States Patent
Kafrawy et al.

(10) Patent No.: US 6,192,568 B1
(45) Date of Patent: Feb. 27, 2001

(54) METHOD OF MAKING AN INTRAVENOUS CATHETER ASSEMBLY

(75) Inventors: Adel Kafrawy, Kingston, MA (US); Fidelis C. Onwumere, Mansfield, TX (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/267,225

(22) Filed: Mar. 11, 1999

(51) Int. Cl.[7] .......................... B29C 45/06; B29C 55/22; B29C 69/02; A61M 25/16; A61M 25/06

(52) U.S. Cl. .................... 29/412; 29/428; 29/430; 264/78; 264/157; 264/159; 264/288.4; 264/291; 264/296; 264/297.3; 264/297.5; 264/328.1; 264/328.8; 264/328.11

(58) Field of Search ..................... 264/157, 159, 264/280, 288.4, 291, 296, 297.3, 328.1, 328.8, 328.11, 78, 297.5; 29/412, 428, 430

(56) References Cited

U.S. PATENT DOCUMENTS

| | | | |
|---|---|---|---|
| 3,406,685 | * | 10/1968 | May . |
| 3,470,604 | * | 10/1969 | Zenick ..................... 29/447 |
| 3,983,203 | * | 9/1976 | Corbett ................... 264/150 |
| 4,212,204 | * | 7/1980 | St. Amand ............... 73/425.6 |
| 4,611,382 | * | 9/1986 | Clark ...................... 29/450 |
| 4,722,344 | | 2/1988 | Cambron et al. ......... 128/658 |
| 4,801,419 | * | 1/1989 | Ward et al. .............. 264/288.4 |
| 4,877,394 | * | 10/1989 | McFarlane ............... 425/567 |
| 5,053,004 | * | 10/1991 | Markel et al. ............ 604/43 |
| 5,087,394 | * | 2/1992 | Keith ....................... 204/22 |
| 5,209,882 | * | 5/1993 | Hattori et al. ............ 264/40.2 |
| 5,409,644 | | 4/1995 | Martin et al. ............ 264/25 |
| 5,531,715 | | 7/1996 | Engelson et al. ......... 604/265 |
| 5,547,364 | * | 8/1996 | Wong et al. .............. 425/384 |
| 5,620,639 | | 4/1997 | Stevens et al. ........... 264/85 |
| 5,741,458 | * | 4/1998 | Rowley .................... 264/494 |
| 5,780,073 | * | 7/1998 | Chen et al. ............... 425/289 |

FOREIGN PATENT DOCUMENTS

| | | | |
|---|---|---|---|
| 3825488 A1 | * | 2/1990 | (DE) .................. A61M/5/158 |
| 2230702A | | 4/1990 | (GB) . |
| 90/00960A1 | | 7/1989 | (WO) . |
| 91/14473A1 | | 3/1990 | (WO) . |

OTHER PUBLICATIONS

European Search Report Mailed Jul. 13, 2000.

* cited by examiner

*Primary Examiner*—Jan H. Silbaugh
*Assistant Examiner*—Michael I. Poe
(74) *Attorney, Agent, or Firm*—Blakely, Sokoloff, Taylor & Zafman (57) ABSTRACT

A method is provided for making a combination hub and catheter. A material is molded in a mold into a body having at least a first hub, and at least a first nose extending from the first hub. The first nose is then elongated into a catheter by moving first and second components of the mold away from one another.

13 Claims, 5 Drawing Sheets

METHOD OF MAKING AN INTRAVENOUS CATHETER ASSEMBLY

BACKGROUND OF THE INVENTION

1). Field of the Invention

This invention relates to a method of making a combination hub and catheter, and to an intravenous catheter assembly.

2). Discussion of Related Art

Catheter assemblies are frequently used for passing fluids between a device such as a syringe or a drip to or from body lumens such as veins or arteries, or other internal target sites. Such an assembly usually includes a hub, a catheter, and a needle. An eyelet ring is usually inserted into the catheter. The catheter, together with the eyelet ring, is then inserted into an opening in a nose of the hub and is secured to the hub by press fitting the eyelet ring within the nose of the hub. A needle is then inserted into the catheter. A sharp tip of the needle is used for piercing a body lumen so that access can be gained into the body lumen by the catheter and the needle. Once the catheter and the needle are located within the body lumen, the needle is removed. A syringe or a pipe of a drip is then attached to the hub so that fluids can be passed through the hub and the catheter between the drip or the syringe and the body lumen.

The hub is usually made of a material providing sufficient rigidity thereto and the catheter is usually made of a material which is flexible, at least when inserted into a body lumen and when exposed to moisture within the body lumen.

The above described method by which the catheter is attached to the hub is cumbersome and expensive and requires complex assembly machines.

SUMMARY OF THE INVENTION

According to one aspect of the invention a method is provided for making a combination hub and catheter. A material is molded into a body having at least a first hub, and at least a first nose extending from the first hub. The first nose is then elongated into a catheter.

The hub may have a luer lock formation thereon.

The catheter may have a length of at least 12 mm, more preferably at least 18 mm, and more preferably at least 30 mm.

The catheter may have an outer diameter of between 0.37 mm and 3.7 mm.

The catheter is preferably sufficiently flexible so as to substantially conform to a curved body lumen when inserted into the body lumen.

The material may be a polyamide such as a nylon, a blend of acrylonitrile/butadiene/styrene and polyurethane, polyetheramide, polypropylene, ethylene propylene copolymers, polyurethane or a blend of a polyamide and a polyetheramide.

The nose is preferably elongated at a temperature wherein the material is malleable.

The catheter is preferably rigid at room temperature and flexible when exposed to moisture and body temperature.

The body preferably has a second hub, and a second nose extending from the second hub, wherein an end of the first nose distant from the first hub is joined with an end of the second nose distant from the second hub, and both the first nose and the second nose are elongated, respectively, into a first catheter and a second catheter. The method may further include the step of severing the first and second catheters from one another.

A plurality of the bodies may be molded simultaneously and the first nose and the second nose of each of the plurality of bodies may simultaneously be elongated.

The bodies may be molded in a mold which is mounted to a turntable and the turntable is rotated so that the mold is at a first station. The method may include the step of rotating the turntable so that the mold is moved to a second station where the first nose and the second nose of each of the plurality of bodies are elongated.

The method may include the steps of rotating the turntable so that the mold is moved to a third station, and ejected the bodies from the mold while the mold is at the third station.

The invention also provides a mold for making a combination hub and catheter, the mold including a first component, and a second component. The first and second components define a volume into which a material can be injected so that the material takes the shape of a hub and nose. The hub may be connected to the first component and the nose connected to the second component so that the nose is elongated into a catheter when the first and second components are moved away from one another.

The volume may include a first hub volume in the first component, a second hub volume in the second component, and a nose passage from the first hub volume to the second hub volume. The material in the nose passage may be elongated when the first and second components are moved away from one another.

The first and second components may define a plurality of these volumes.

The invention further provides an intravenous catheter assembly which includes a hollow hub, a catheter, and a needle. The catheter has a length of at least 12 mm, a first end which is secured to the hub in a unitary construction, a second end distant from the hub, and a passage extending from the hub out of the second end. The needle is removably located within the passage and has a sharp tip in proximity to the second end of the catheter.

The hub and the catheter are preferably made of the same material.

BRIEF DESCRIPTION OF THE DRAWINGS

The invention is further described by way of examples with reference to the accompanying drawings wherein.

DETAILED DESCRIPTION OF THE INVENTION

Figure 1:
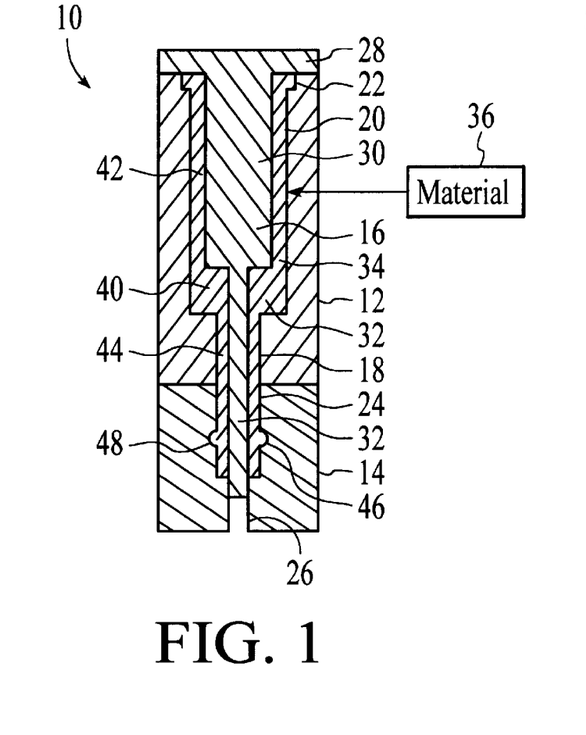
FIG. 1 is a sectioned side view of a mold which is used for making a combination hub and catheter according to an embodiment of the invention.

FIG. 1 of the accompanying drawings illustrates a mold 10 which is used for making a combination hub and catheter. The mold 10 includes a first component 12, a second component 14, and a core pin 16.

The first component 12 has an opening formed therein with a lower portion, or first nose volume, 18 having a relatively small diameter, and an upper portion, or hub volume, 20 having a relatively large diameter. The upper portion 20 is slightly enlarged at a mouth 22 at a top thereof.

An opening is formed in the second component having an upper portion, or second nose volume, 24 which has a diameter which is the same size as the lower portion 18 in the first component 12, and a lower portion 26 which is smaller than the upper portion 24. The second component 14 is located below the first component 12 and is positioned so that surfaces of the first and second components 12 and 14 contact one another and the lower portion 18 in the first component 12 is aligned with the upper portion 24 in the second component 14.

The core pin 16 has a base portion 28, a stem portion 30 extending from the base portion, the stem portion 30 having a relatively large diameter, and a pin portion 32 extending from the stem portion 30, the pin portion 32 having a relatively small diameter when compared to the stem portion 30. The pin portion 32 is inserted into the upper portion 20 in the first component 12 and from there into the lower portion 18 of the first component 12, the upper portion 24 of the second component 14 and through the lower portion 26 of the second component 14 so that the pin portion 32 protrudes out of the second component 14. The stem portion 30 is so located within the upper portion 20 in the first component 12. The first and second components 12 and 14 together with the core pin define a volume 34 around the core pin and within the openings in the first and second components 12 and 14, but excluding between the pin portion 32 and lower portion 26 in the second component 14.

A material 36 is injected into the volume 34 so that the material 36 fills the volume 34. The material 36 is above its melting point and above room temperature, and is preferably also color coded.

The material within the volume 34 is then allowed to cool to a temperature below the melting point of the material, but still above a temperature when the material becomes malleable and above room temperature. A malleable body 40 is so molded within the mold 10, the body 40 having a hub 42 and a nose 44 extending from the hub 42. The hub 42 is formed within the upper portion 20 in the first component 12 and the nose 44 is formed in the lower portion 18 in the first component 12 and in the upper portion 24 in the second component 14. An enlargement or a notch 46 is formed low down within the upper portion 24 in the second component 14 and the material fills the notch 46 so that the nose 44 has a rib 48 located within the notch 46.

Figure 2:
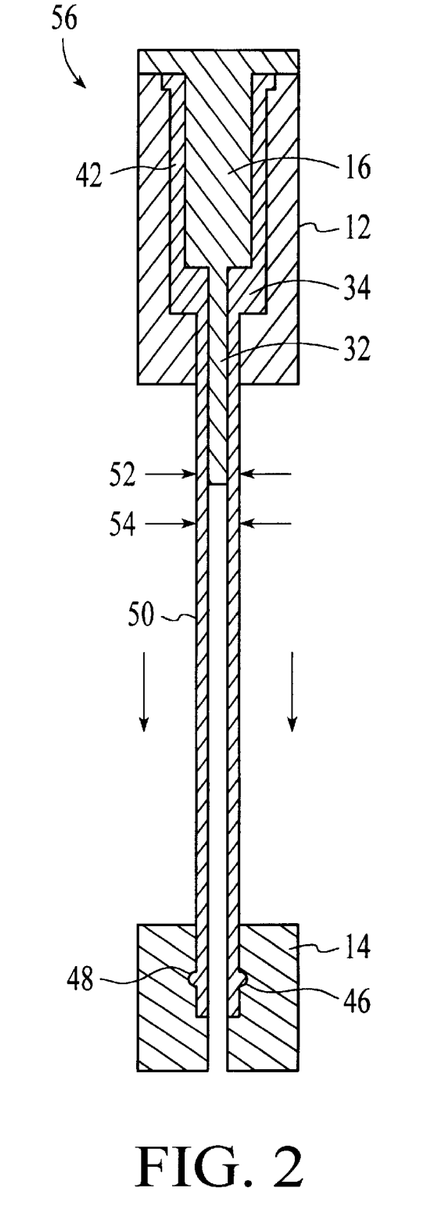
FIG. 2 is a view similar to FIG. 1 after a second component of the mold is moved relative to a first component thereof to stretch a nose of a body, formed by the mold in FIG. 1, into a catheter.

As illustrated in FIG. 2, the second component 14 is then moved away from the first component 12 along the pin portion 32 while the material is still in a malleable condition. The rib 48 engages within the notch 46 so that the nose 44 of FIG. 1 is elongated or stretched into a catheter 50. An outer diameter of the nose 44 reduces in size while it is being elongated into the catheter 50 to form an outer diameter 52 of the catheter 50. An inner diameter 54 of the catheter 50 is generally determined by the outer diameter of the pin portion 32.

The outer diameter 54 can also be more accurately controlled by controlling the rate at which the catheter 50 is stretched and by heating or cooling the catheter 50 while being formed. The catheter 50 can also be selectively heated or cooled at different locations along the length thereof while being formed in order to influence the diameters 52 and 54 selectively over the length of the catheter. For example, by maintaining a lower portion of the catheter 50 at a lower temperature than the remainder of the catheter 50, the lower portion can have an outer diameter which is smaller than an upper portion of the catheter 50, so that an outer surface of the catheter tapers inward towards a lower end thereof, or which is beveled.

Figure 3:
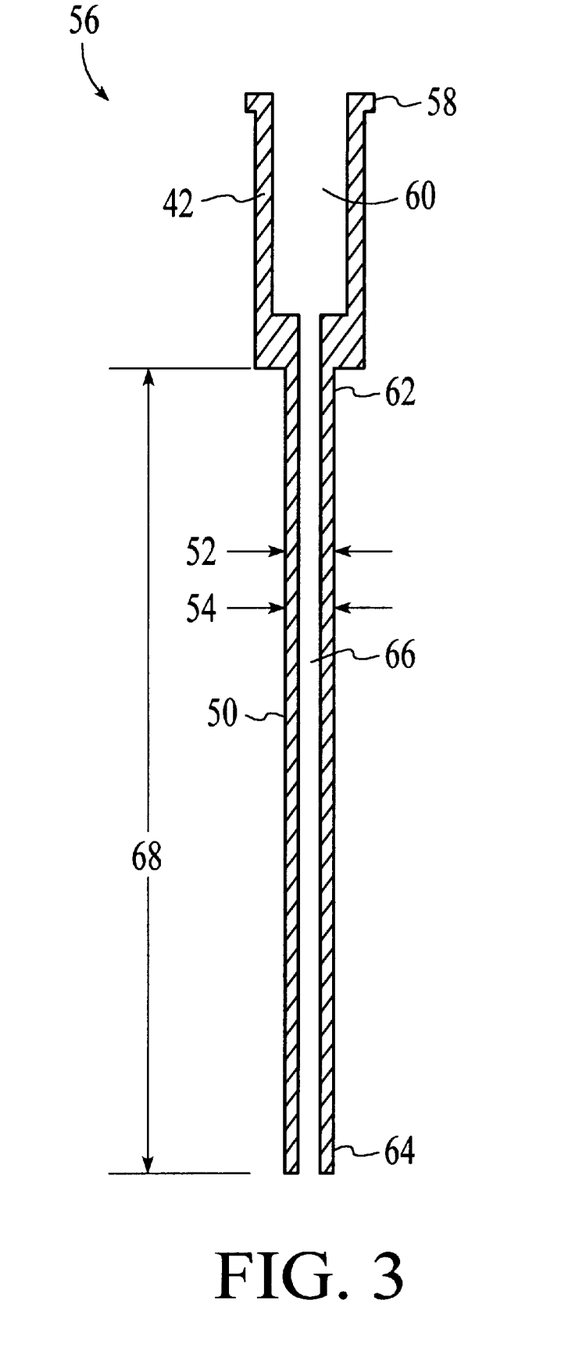
FIG. 3 is a sectioned side view of a combination hub and catheter which is made according to the method illustrated in FIG. 1 and FIG. 2.

The second component 14 is then released from the catheter 50. The core pin 16 is pulled out of the catheter 50 and the hub 42. The pin portion 32 extends only a short distance into the catheter 50, thus facilitating its release from the catheter 50. The hub 42 and catheter 50 are then removed from the first component 12. A combination hub and catheter 56 as illustrated in FIG. 3 is so provided which includes a hub 42 and a catheter 50. The combination hub and catheter 56 is then allowed to cool to room temperature which is below the temperature when the material becomes malleable. A primary advantage is that the combination hub and catheter 56 is made according to an easy, inexpensive method which does not require assembly of a catheter and a hub utilizing complex equipment or assembly procedures.

The hub 42 has a luer lock formation 58 on a side thereof opposing the catheter 50, and a first passage 60 therethrough.

The catheter 50 has a first end 62 which is secured to the hub 42 in a unitary construction in the sense that the hub 42 and the catheter 50 are made of a single component, i.e. without an interface between one component of which the hub 42 is made and another component of which the catheter 50 is made. The catheter 50 is cut off just above the rib 48 to rid the catheter 50 of the rib 48. A second end 64 of the catheter 50 is located distant from the hub 42. A second passage 66 is formed through the catheter 50 and extends from the first passage 60 in the hub 42, through the catheter 50 out of the second end 64. The catheter 50 has an outer diameter 52, an inner diameter 54, and a length 68. The material of the combination hub and catheter 56 is color coded, the color of the combination hub and catheter 56 depending on the gauge of the catheter 50. Specifications of different combinations hub and catheters are recited in the table which follows wherein dimensions are given in millimeters.

TABLE

| Outer diameter 52 | Inner diameter 54 | Length 68 | Color |
|---|---|---|---|
| 2.13 | 1.75 | 31 | Orange |
| 2.13 | 1.75 | 56 | Orange |
| 1.70 | 1.38 | 31 | Gray |
| 1.70 | 1.38 | 56 | Gray |
| 1.28 | 0.98 | 44 | Green |
| 1.28 | 0.98 | 31 | Green |
| 1.10 | 0.80 | 31 | Pink |
| 1.10 | 0.80 | 25 | Pink |
| 1.10 | 0.80 | 44 | Pink |
| 0.83 | 0.63 | 25 | Blue |
| 0.70 | 0.50 | 19 | Yellow |

Figure 4:
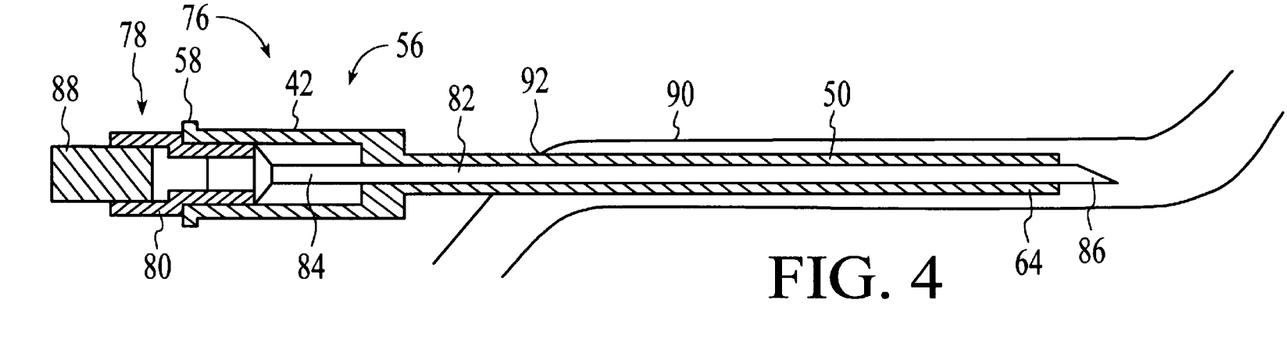
FIG. 4 illustrates an intravenous catheter assembly, which includes the combination hub and catheter, after being inserted into a body lumen.

FIG. 4 illustrates an intravenous catheter assembly 76 according to an embodiment of the invention which includes the combination hub and catheter 56, and a needle product 78. The needle product 78 includes a body, a fluid detecting transparent chamber 80 and a needle 82. The needle has a first end 84 which is secured to the chamber 80, and a second end 86, having a sharp tip located distant from the chamber 80. A passage is formed through the needle 82 and is in communication with the confines of the chamber 80. A porous plug 88 closes an open end of the chamber 80 opposing the needle 82. The second end 86 is inserted first into the hub 42, and from the hub 42 through the catheter 50 until the second end 86 protrudes from the second end 64 of the catheter 50, while still being in proximity to the second end 64 of the catheter 50.

In use, the second end 86 of the needle 82 is used to pierce a body lumen 90 such as a vein or an artery so that an opening 92 is formed into the body lumen 90. The catheter 50 is then inserted together with the needle 82 into the body lumen 90 through the opening 92. As mentioned, the catheter may be tapered or beveled at its second end 86. Because of the tapered or beveled second end 86, the catheter may more easily enter the lumen 90 than may otherwise be possible. The plug 88, due to its porosity, allows for venting of air from within the chamber 80 to allow for fluid within the lumen 90 to flow through the needle 82 into the chamber 80 where the fluid is visible through a wall of the chamber 80.

Figure 5:
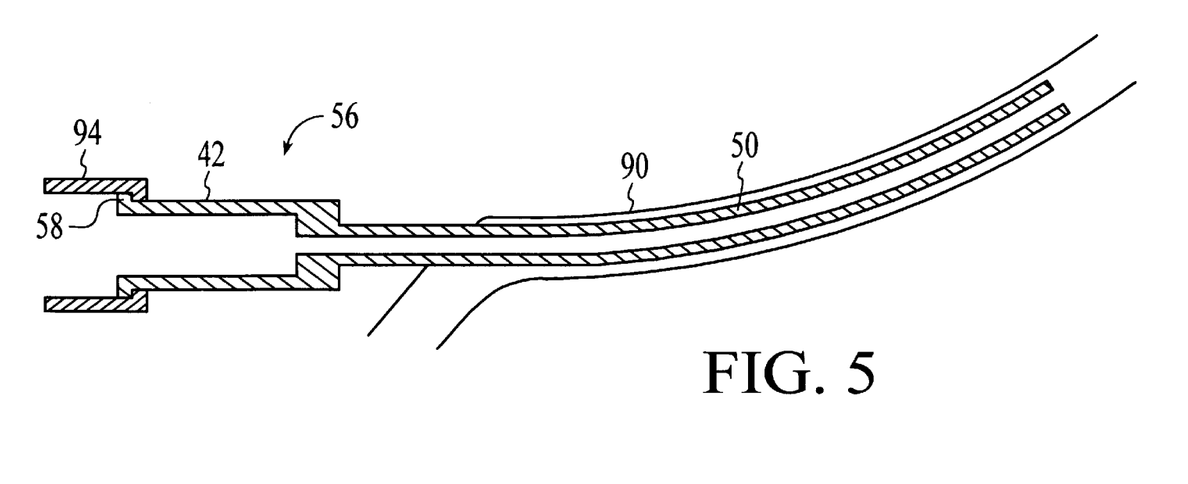
FIG. 5 illustrates the combination hub and catheter after a needle product of the assembly of FIG. 4 is removed therefrom and the catheter of the combination hub and catheter substantially conforms to a natural shape of the body lumen.

As illustrated in FIG. 5, the needle product 78 of FIG. 4 is then removed from the combination hub and catheter 56. Another device 94 such as a syringe or a pipe of a drip is then connected to the luer lock formation 58. Fluids can then be passed through the hub and the catheter 50 between the body lumen 90 and the device 94.

The lumen 90 may be naturally curved, as illustrated in FIG. 5. The catheter 50 is preferably made of a material which is relatively strong when inserted into the lumen, but should preferably be sufficiently flexible so as to substantially conform to the natural shape of the body lumen 90 when inserted into the body lumen 90 and the needle 82 is removed. As will be discussed herein below, certain materials are rigid at room temperature and in dry conditions, but are hydrophilic so that the catheter 50 becomes sufficiently flexible when exposed to warmer temperatures and moisture generally found within a lumen. The material of the catheter 50 should also preferably allow for at least 24 hours, more preferably up to 72 hours of indwelling. Since the hub 42 and the catheter 50 are made of the same material, the materials should still be strong enough to provide the necessary rigidity to the hub 42.

One material which can be used for making the combination hub and catheter 56 is a polyamide such as nylon 6, nylon 66, nylon 11 or nylon 12. A polyamide is also easily molded and can be easily stretched. A polyamide is also a material which can be easily colored. A combination hub and catheter as hereinbefore described which is made of a polyamide has a hub which is sufficiently rigid when ribs or other strengthening formations are formed on the hub, and a catheter which is sufficiently flexible to conform to the shape of a curved body lumen. A polyamide, in particular, is hydrophilic so that it becomes more flexible when exposed to heat and moisture.

Another material which can be used for the combination hub and catheter 56 hereinbefore described is a blend of acrylonitrile/butadiene/styrene resin (ABS) and polyurethane, such as a material which is sold under the name PREVAIL 3050, PREVAIL 3100, or PREVAIL 3150 by Dow Chemicals of Midland, Michigan. PREVAIL can be easily colored, molded and stretched. A hub made of PREVAIL is sufficiently rigid when ribs or other strengthening formations are formed on the hub, and a catheter formed of PREVAIL is sufficiently flexible to conform to the shape of a curved body lumen. PREVAIL, in particular, is hydrophilic so that it becomes more flexible when exposed to moisture and heat.

Another material which can easily be molded and stretched is fluorinated ethylene propylene copolymers (FEP). FEP is also sufficiently flexible to conform to the shape of a curved body lumen. FEP provides a hub which is sufficiently rigid, and a catheter which is hydrophilic so as to become flexible when exposed to moisture and heat. Other materials mentioned herein are, however, more easily color coded than FEP.

Another material which may be used for a combination hub and catheter 56 as hereinbefore described is polyurethane. Polyurethane provides a hub which is sufficiently rigid when ribs and other strengthening formations are provided on the hub, and a catheter which is generally sufficiently flexible for purposes of forming a sufficiently flexible catheter. Polyurethane is also hydrophilic so as to become more flexible when exposed to heat and moisture. Polyurethane can also be easily color coded, molded and stretched.

Another material which may be used for making a combination hub and catheter 56 of the kind herein before described is a polyetheramide such as sold under the name PEBAX by Elf Atochem of Philadelphia, Pa. PEBAX has similar characteristics to nylon.

Polypropylene may also be used for making a combination hub and catheter of the afore described kind. Polypropylene generally has sufficient stiffness for purposes of providing rigidity to a hub of such a combination hub and catheter. A catheter which is formed of polypropylene will generally be relatively stiff, but may suffice for particular purposes.

Other materials which may be used are ethylene propylene co-polymers. Such co-polymers have similar characteristics as ethylene and propylene hereinbefore described and, depending on ratios of ethylene to propylene used, provide hubs which are sufficiently rigid and catheters which are sufficiently flexible.

Another material which may be used is a blend of PEBAX and a polyamide which, depending on the blend which is used, may provide some characteristics of PEBAX which are superior to a polyamide and other characteristics of polyamide that are superior to PEBAX.

Figure 6:
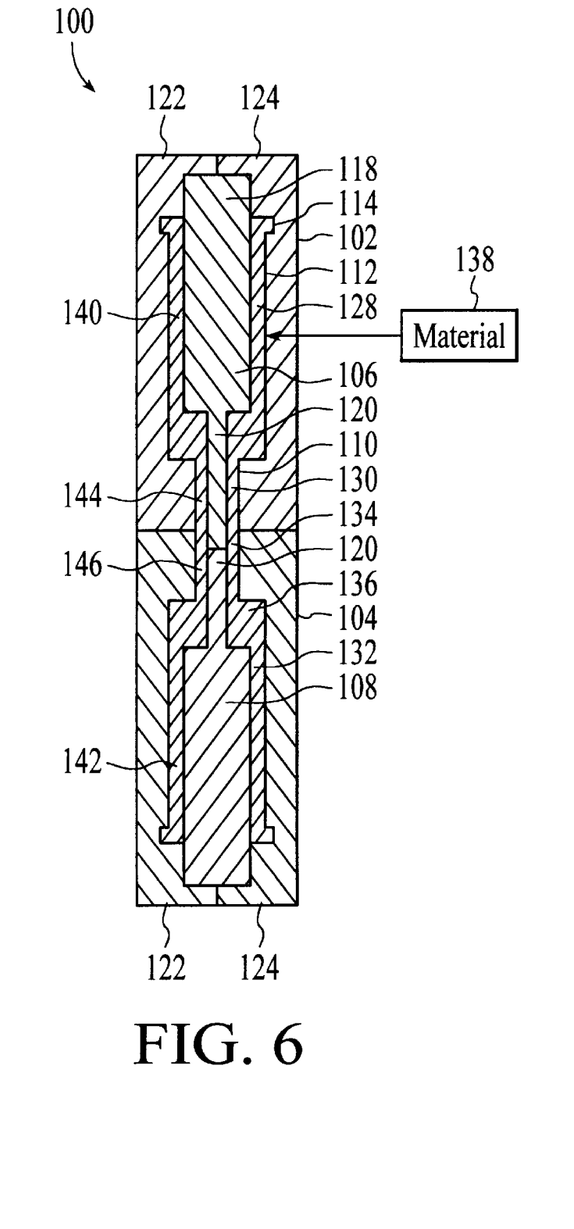
FIG. 6 is a sectioned side view of a mold which is used for making two combinations hub and catheter according to another embodiment of the invention.

FIG. 6 illustrates another mold 100 which may be used for making two combinations hub and catheter. The mold 100 includes a first component 102, a second component 104, a first core pin 106, and a second core pin 108.

The first component 102 has an opening formed therein with a lower portion 110 having a relatively small diameter, and an upper portion 112 having a relatively large diameter. The upper portion 112 is slightly enlarged at an upper end 114 thereof.

The first core pin has a stem portion 118 having a relatively large diameter, and a pin portion 120 extending from the stem portion, the pin portion 120 having a relatively small diameter when compared to the stem portion 118.

The first component 102 includes first and second parts 122 and 124 which jointly define an enclosure which is open only at the lower portion 110. In order to locate the first core pin 106 within the first component 102, the first and second parts 122 and 124 thereof are moved apart. The first core pin 106 is then inserted and the first and second parts 122 and 124 are again moved against one another so that the first core pin 106 is located within the first component 102.

A first hub volume 128 and a first nose volume 130 are defined by the first component 102 and the first core pin 106.

The second component 104 and the second core pin 108 have exactly the same constructions as the first component 102 and the first core pin 106 respectively. A second hub volume 132 and a second nose volume 134 are defined by the second component 104 and a second core pin 108.

The first and second components 102 and 104 are initially located next to one another so that the first and second nose volumes 130 and 134 are located over one another and the pin portions 120 of first and second core pins 106 and 108 contact one another. A volume 136 is thereby defined which includes the first and second hub volumes 128 and 132, and a nose passage defined by the first and second nose volumes 130 and 134 jointly. A material 138 is injected into the volume 136 so that the material 138 flows into the hub volumes 128 and 132 and the nose volumes 130 and 134.

The material within the volume 136 is allowed to solidify, thereby forming a body having a first hub 140 in the first hub volume 128, a second hub 142 in the second hub volume 132, a first nose 144 in the first nose volume 130, and a second nose 146 in the second nose volume 134.

Figure 7:
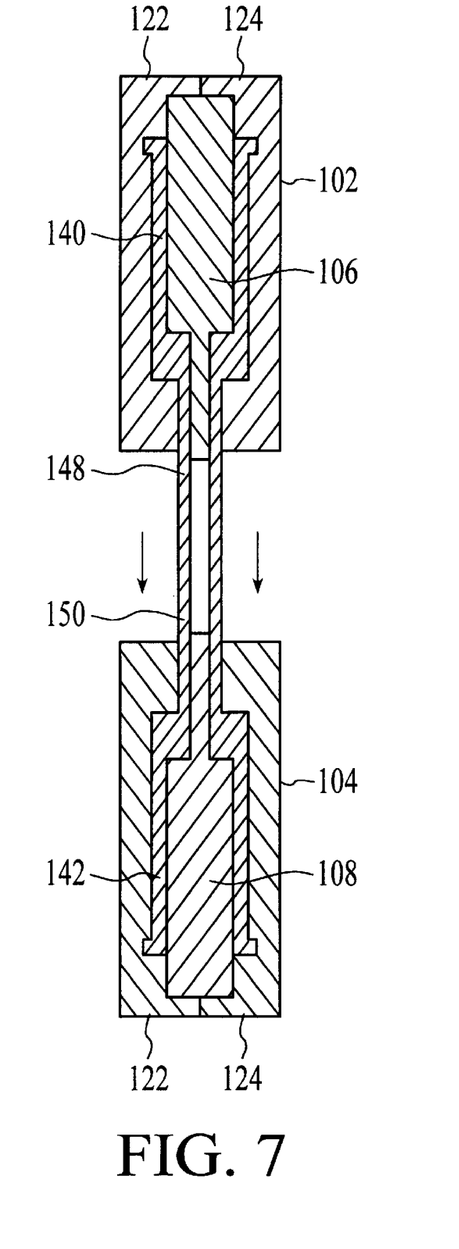
FIG. 7 is a view similar to FIG. 6 after the second component of the mold is moved relative to a first component thereof to stretch noses of a body, formed in the mold of FIG. 6 into respective catheters.
Figure 8:
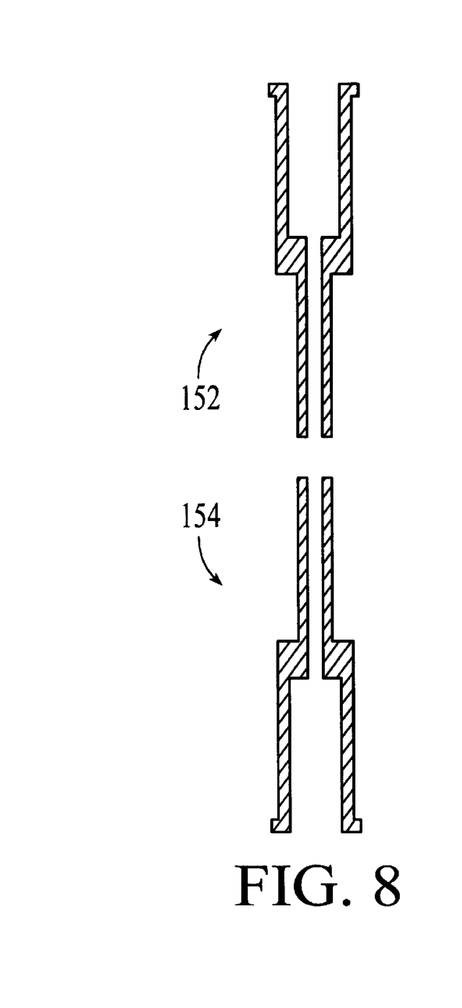
FIG. 8 is a sectioned side view of two combinations hub and catheter which are made according to the method illustrated in FIGS. 6 and 7.

While the material is still malleable, as illustrated in FIG. 7, the first and second components 102 and 104 are moved away from one another. The first nose 144 is elongated into a first catheter 148, and the second nose 146 is elongated into a second catheter 150. Ends of the first and second catheters 148 and 150 are joined to one another. The first and second parts 122 and 124 are then moved away from one another, and the core pins 106 and 108 are removed. The first and second catheters 148 and 150 are then severed from one another to leave two combinations hub and catheter, 152 and 154 respectively, as illustrated in FIG. 8.

Each combination hub and catheter 152 or 154 is the same as the combination hub and catheter 56 as illustrated in FIG. 3. The material used for making the combinations hub and catheter 152 and 154 may be the same as for the combination hub and catheter 56 of FIG. 3, the manner in which the combinations hub and catheter 152 and 154 are made, including the mold used for making them are the same as for the combination hub and catheter 56 of FIG. 3 in all other respects.

Figure 9:
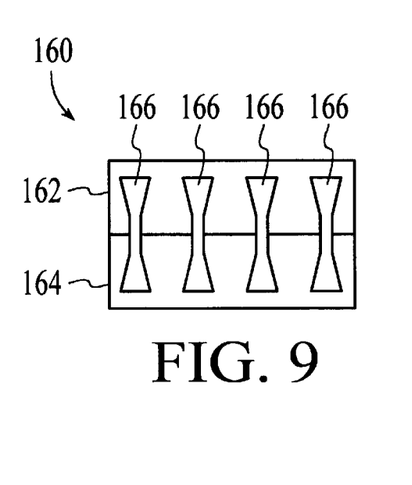
FIG. 9 illustrates a mold in which a plurality of combinations hub and catheter can be made.

FIG. 9 illustrates another mold 160 which includes first and second components 162 and 164 respectively. The mold 160 defines a plurality of volumes 166. Each volume 166 is the same as the volume 136 in FIG. 6. Bodies are simultaneously molded within each of the volumes 166 and the nose portions of all the bodies are then simultaneously elongated. An advantage of using the mold 100 of FIG. 6, and more particularly the mold 160 of FIG. 9, is that more combinations hub and catheter can be manufactured in the same cycle.

Figure 10:
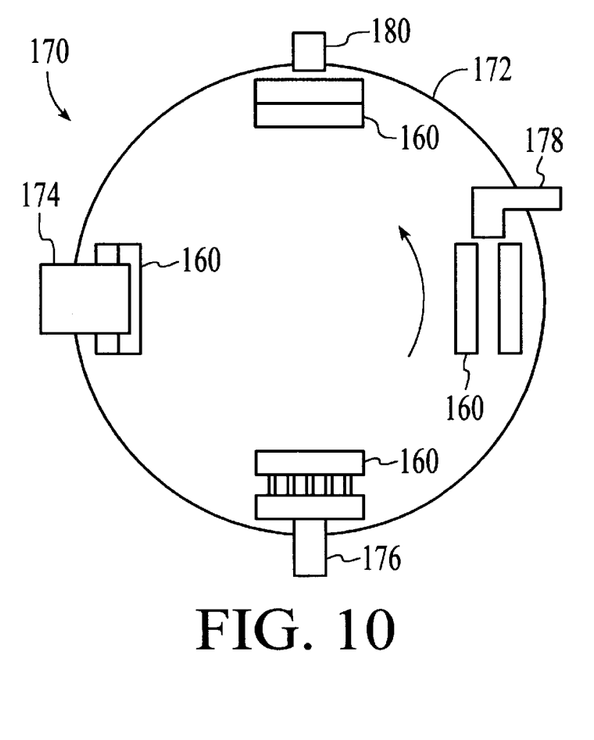
FIG. 10 is a plan view of an apparatus which is used in manufacturing combinations hub and catheter according to the invention.

FIG. 10 illustrates manufacturing apparatus 170 which includes a turntable 172, a mold 160 such as the mold 160 in FIG. 9, an injection molding machine 174, pulling apparatus 176, cutting and ejection apparatus 178, and closing apparatus 180.

The mold 160 is mounted to the turntable 172. The injection molding apparatus 174, the pulling apparatus 176, the cutting and ejection apparatus 178, and the closing apparatus 180, are respectively located at a first, a second, a third, and a fourth station around the turntable 172. The turntable 172 is first rotated so that the mold 160 is at the first station where material is injected into the mold 160. The turntable 172 is then rotated through about 90° so the mold 160 is moved to the second station where the pulling apparatus 176 stretches the nose portions into catheters. The turntable 172 is then again rotated though about 90° to the third station so the cutting and ejection apparatus 178 removes the bodies from the mold 160 and subsequently sever or cut the catheters from one another. The turntable 172 is then again rotated through about 90° until the mold 160 is moved to the fourth station where the closing apparatus 180 again moves the first and second components 162 and 164 of the mold 160 towards one another. The mold 160 is then ready for another injection step at the first station.

In another embodiment the bodies may be removed from the injection molding machine and located in a stretching machine such as an Instron universal testing instrument, to be stretched by the stretching apparatus under conditions that can be optimally controlled.

While certain exemplary embodiments have been described and shown in the accompanying drawings, it is to be understood that such embodiments are merely illustrative and not restrictive of the current invention, and that this invention is not restricted to the specific constructions and arrangements shown and described, since modifications may occur to those ordinarily skilled in the art.

What is claimed is:

1. A method of making an intravenous catheter assembly, which includes:

molding a material into a body having, at least a first hub having a diameter and at least a first malleable nose having a smaller diameter extending from the first hub, in a mold having a first component, a second component and a core pin, the first component connecting to an end of the first, malleable nose at the first hub, the second component connecting to an end of the first, malleable nose distant from the first hub;

moving the first and second components away from one another, thereby elongating the first, malleable nose into a catheter that extends from the first hub; and inserting a needle product into the first hub and the catheter to produce the intravenous catheter assembly, the needle product including a needle and a chamber, the needle having a sharp tip located distant from the chamber, the sharp tip being used for piercing a body lumen so that the catheter assembly with the needle product can be inserted into the body lumen with the first hub located outside the body lumen and the catheter located inside the body lumen, the needle product being removable from the first hub and the catheter while the catheter is located inside the body lumen, the catheter being of a material that is sufficiently flexible so as to substantially conform to a natural shape of the body lumen when the needle product is removed from the first hub and the catheter while the catheter is located inside the body lumen.

2. A method as in claim 1 wherein the first hub has a luer lock formation thereon.

3. A method as in claim 1 wherein the catheter has a length of at least 12 mm.

4. A method as in claim 1 wherein the catheter has a length of at least 30 mm.

5. A method as in claim 1 wherein the catheter has an outer diameter of between 0.37 mm and 3.7 mm.

6. A method as in claim 1 wherein the material is selected from the group comprising a polyamide, a blend of acrylonitrile/butadiene/styrene and polyurethane, polyetheramide, a fluorinated ethylene propylene copolymer, polypropylene, an ethylene propylene copolymer, polyurethane, and a blend of a polyamide and a polyetheramide.

7. A method as in claim 1 wherein the catheter is rigid at room temperature and flexible when exposed to moisture and body temperature.

8. The method of claim 1 comprising making at least two of said intravenous catheter assemblies, a first of said catheter assemblies having a catheter of a first color and a first outer diameter and a second of said catheter assemblies having a second color different from the first color and a second outer diameter different from the first outer diameter.

9. The method as in claim 1 wherein (i) the body has a second hub and a second, malleable nose extending from the second hub such that an end of the first nose which is distant from the first hub is joined with an end of the second nose which is distant from the second hub, and (ii) the first and second components are moved away from one another so that both the first, malleable nose and second, malleable nose are elongated into a first catheter extending from the first hub and a second catheter extending from the second hub, respectively, the method further including:

severing the first and second catheters from one another.

10. The method as in claim 9 which includes:

simultaneously molding a plurality of said bodies in the mold; and simultaneously elongating the first nose and the second nose of each of the plurality of bodies.

11. The method as in claim 10 wherein the mold is mounted to a turntable and the bodies are molded when the turntable is rotated so that the mold is at a first station, the method including:

rotating the turntable so that the mold is moved to a second station where the first nose and the second nose of each of the plurality of bodies are elongated.

12. The method as in claim 11 which includes:

rotating the turntable so that the mold is moved to a third station, the first and second catheters being severed while the mold is at the third station.

13. The method as in claim 11 which includes:

rotating the turntable so that the mold is moved to a third station; and ejecting the bodies from the mold while the mold is at the third station.

* * * * *